United States Patent [19]
Chan

[11] Patent Number: 6,119,477
[45] Date of Patent: Sep. 19, 2000

[54] PORTABLE AIR-COOLING SYSTEM

[76] Inventor: Stephen Chan, 3573 Napier Street, Vancouver, British Columbia, Canada, V5K 2X8

[21] Appl. No.: 09/275,971

[22] Filed: Mar. 25, 1999

Related U.S. Application Data

[63] Continuation-in-part of application No. 08/959,880, Oct. 29, 1997, abandoned.

[51] Int. Cl.[7] ........................................ F25D 17/04
[52] U.S. Cl. ......................... 62/406; 62/457.2; 62/457.3
[58] Field of Search .................. 62/406, 457.2, 62/457.3, 293, 238.1

[56] References Cited

U.S. PATENT DOCUMENTS

| | | | |
|---|---|---|---|
| 5,046,329 | 9/1991 | Travis | 62/406 X |
| 5,062,281 | 11/1991 | Oliphant et al. | 62/406 X |
| 5,953,933 | 9/1999 | Cheng | 62/457.2 X |

Primary Examiner—William Doerrler
Assistant Examiner—Chen-Wen Jiang

[57] ABSTRACT

A portable cooling system has a drink container with a drink inlet opening in the top of the container, a removable closure closing the opening and a chilled drink in the drink container. An air duct extends through the drink in the container to the exterior of the container. A battery-driven air blower is attached to the container and forms therewith a portable device and the battery-driven blower has an air outlet connected to the air duct, which extends upwardly through the removable closure to the exterior of the drink container. A drinking tube extends from the exterior of the container into the chilled drink.

14 Claims, 5 Drawing Sheets

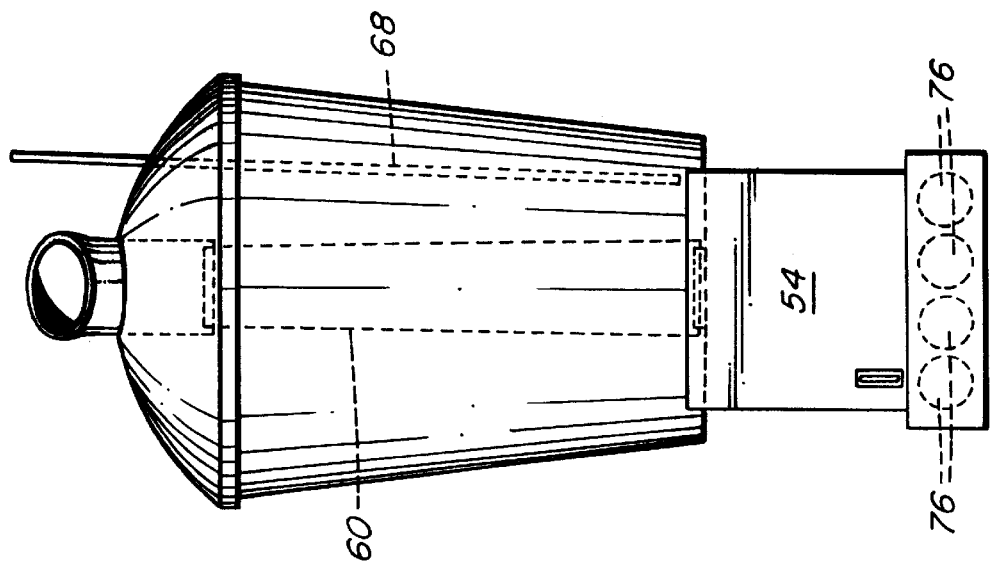
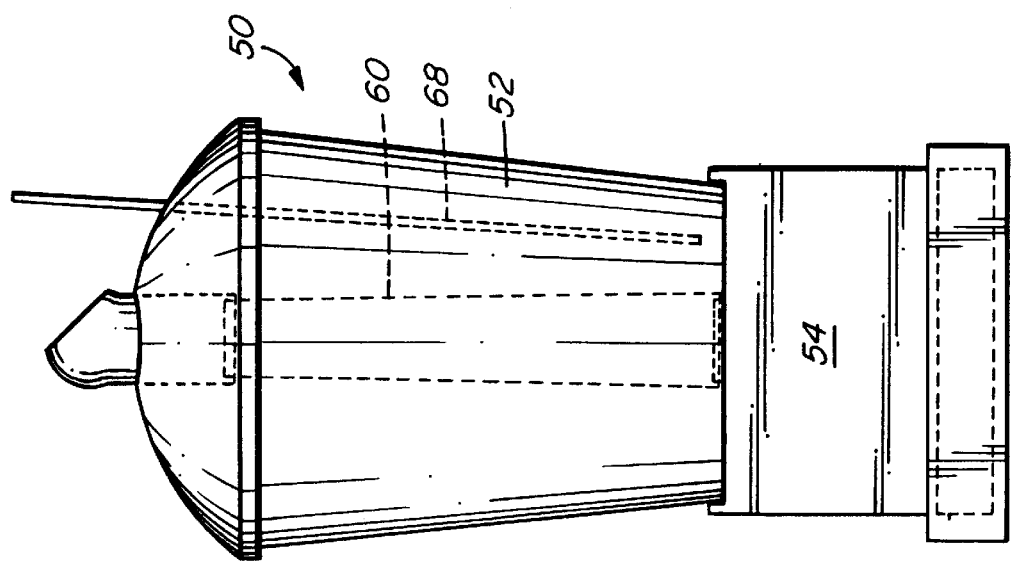

PORTABLE AIR-COOLING SYSTEM

CROSS-REFERENCE TO RELATED APPLICATION

This is a continuation-in-part of patent application Ser. No. 08/959,880, filed Oct. 29, 1997, now abandoned.

BACKGROUND OF THE INVENTION

1. Field of the Invention

The present invention relates to a portable cooling system and, more particularly, to a system for supplying and discharging a flow of cooling air onto the body of a user of the system while the system is carried by the user.

2. Description of the Related Art

In the past, various systems have been proposed for cooling a user's body. For example, U.S. Pat. No. 4,914,752, issued Apr. 10, 1990 to Thomas L. Hineson et al., proposes a garment for receiving temperature regulated air from an external air source in the form of an air compressor, which is connected to the garment through a vortex tube, for cooling the air, and a diffusing layer, a control valve being adjustable for controlling the coldness of the air discharged from the vortex tube.

U.S. Pat. No. 5,320,164, issued Jun. 14, 1994 to Stephen P. Szczesuil et al., describes a body heating/cooling garment which utilizes fluid-carrying tubes and provides both air and vapour permeability to promote convective heat transfer, while also providing conductive heat transfer, with a heating/cooling unit connected to the garment through an umbilical connection line.

BRIEF SUMMARY OF THE INVENTION

The present invention is based on an appreciation of the fact that cooling of a user of the present system should usefully combine the provision of a chilled drink, together with a discharge of cooling air onto the user's body.

More particularly, according to the present invention there is provided a portable cooling system, comprising a drink container having a drink inlet opening in the top of the container and a removable closure closing the opening, a chilled drink in the drink container and an air duct extending through the drink in the container to the exterior of the container. A battery-driven air blower attached to the container forms therewith a portable device and has an air outlet connected to the air duct and the air duct extends upwardly through the removable closure to the exterior of the drink container. A drinking tube extends from the exterior of the container into the chilled drink.

In a preferred embodiment of the invention there is provided a base unit containing the battery driven air blower, the drink container having a bottom mounted on the base unit, and interengageable formations on the base unit and the bottom of the drink container for releasibly securing the base unit to the drink container, and the air duct having an open lower end communicating with the air blower outlet opening through the drink container bottom. An air freshener material is provided in the air duct and the air duct is provided at an upper end thereof with a rotatable air discharge outlet.

BRIEF DESCRIPTION OF THE DRAWINGS

The invention will be more readily understood from the following description of a preferred embodiment thereof given, by way of example, with reference to the accompanying drawing, in which:

FIG. 4 shows a view in front elevation of a portable cooling system according to another embodiment of the present invention; and FIG. 5 shows a view in side elevation of the cooling system of FIG. 4;

DESCRIPTION OF THE PREFERRED EMBODIMENTS

Figure 1:
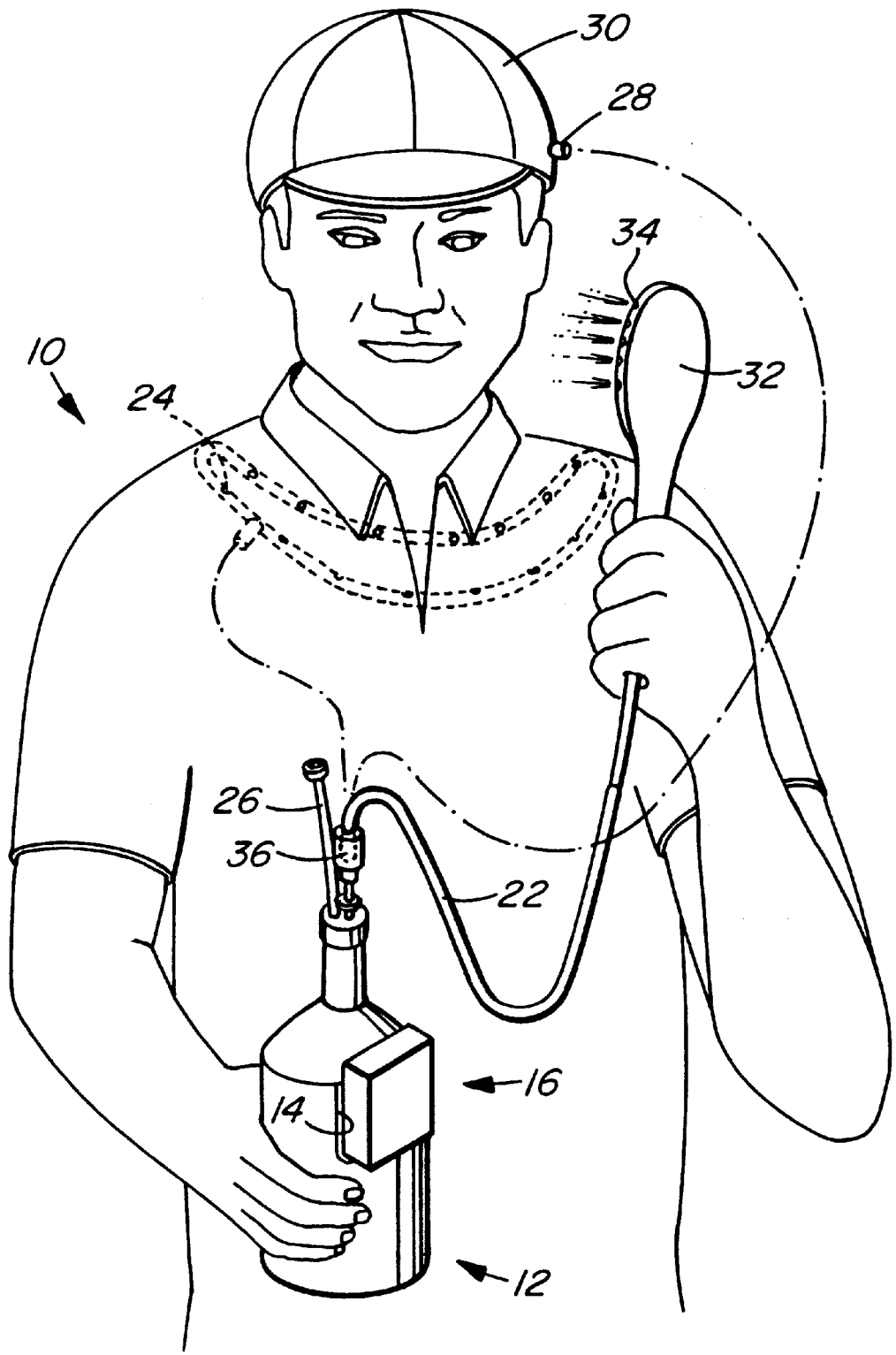
FIG. 1 shows a view of a user provided with a cooling system according to the present invention.
Figure 2:
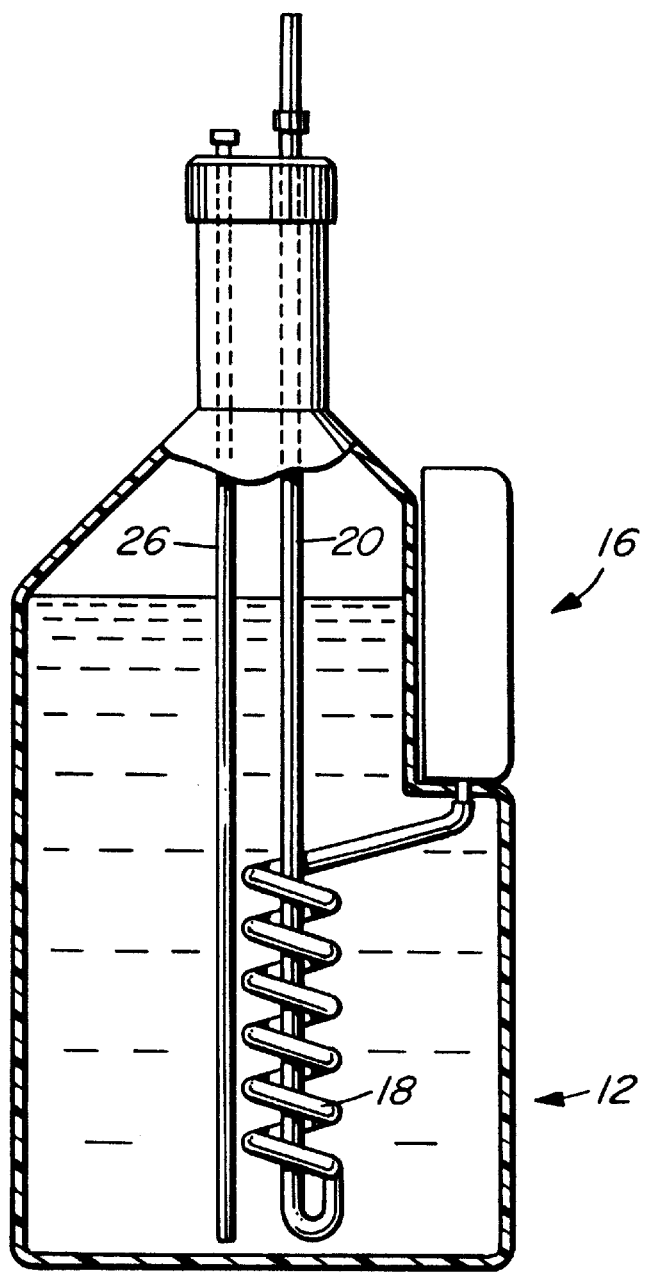
FIG. 2 shows a view taken in vertical cross-section through a beverage container forming part of the system of FIG. 1.
Figure 3:
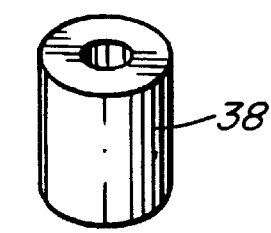
FIG. 3 shows view in perspective of an air freshener for use in the air cooling system of FIG. 1.

In the accompanying drawing, reference numeral 10 indicates a person provided with a cooling system, which comprises a drink container indicated generally by reference numeral 12.

The exterior of the drink container 12 is formed with a recess 14 shaped to receive an air blower/battery pack indicated generally by reference numeral 16.

The air blower/battery pack 16 provides an air flow to a helical coil of heat exchanger tubing 18 in the interior of the container 12. The heat exchanger tubing 18 is connected through a straight outlet pipe 20 to an air duct tubing 22 which, in the present embodiment of the invention, is connected to an air outlet in the form of a perforated necklace tubing 24 which, as shown, is fitted over the head and onto the shoulders, the back and the chest of the use 10 and which serves to supply a discharge of cooling air onto the user 10.

In operation of this system, a chilled drink, for example plain water, soda water or fruit juice, is provided in the container 12. On operation of the air blower/battery pack 16, air supplied through the heat exchanger tubing 18 is cooled by this chilled drink before the air is passed through the air duct tubing 22 to the air outlet necklace 24.

The container 12 is provided with a drinking straw 26, through which the user 10 can drink the contents of the container 12.

If required, a perforated outlet tubing, a portion of which is indicated by reference numeral 28, may be secured within a hat 30 or another article of clothing for use by the user 10. A further possibility is to connect the air duct tubing to a paddle-like air outlet 32, provided with a plurality of air outlet holes 34, in which case the user 10 can grip and manipulate the air outlet paddle 32 so as to direct a flow of cooling air onto any portion of his or her body or onto a companion or elsewhere.

The air duct tubing 22 is provided with an air freshener housing 36, which contains a cylindrically-shaped air freshener 38, containing a perfume for freshening the air discharged onto the user.

In FIG. 4 of the accompanying drawings, there is shown a portable cooling system, indicated generally by reference numeral 50, according to a second embodiment of the present invention.

The cooling system 50 comprises an upper portion in the form of a container 52, defining in its interior a space for containing a beverage or drink, and a bottom portion 54 in the form of a base unit, upon which the container 52 is releasably mounted.

Figure 8:
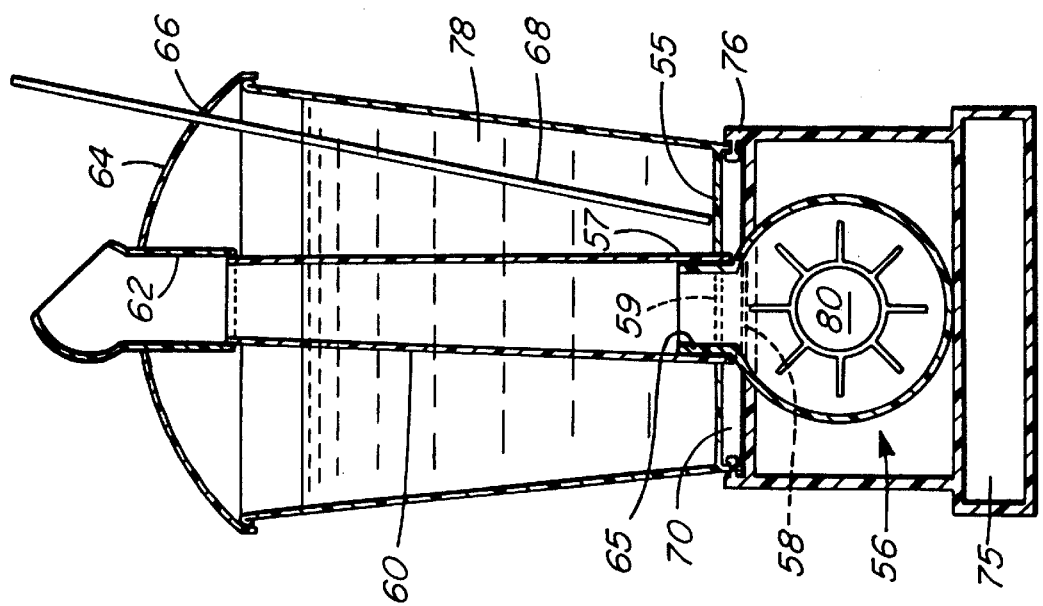
FIG. 8 shows a view taken in vertical cross-section through the portable cooling system of FIG. 4.
Figure 6:
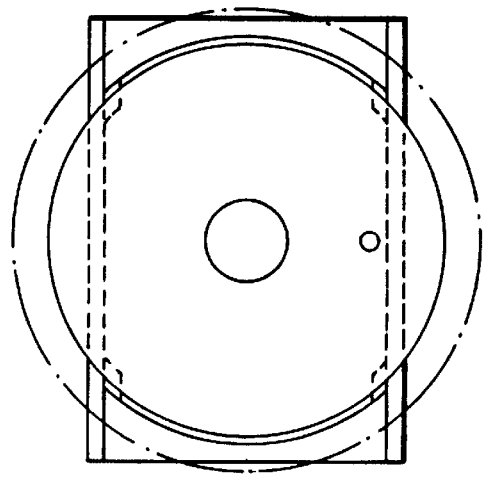
FIG. 6 shows a plan view of the cooling system of FIG. 4.
Figure 7:
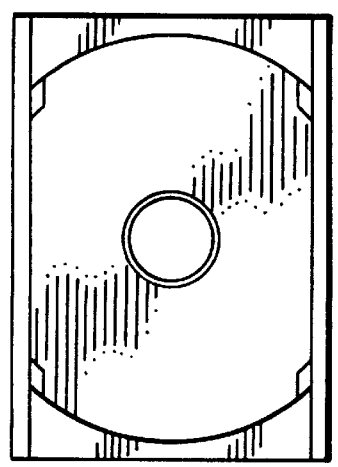
FIG. 7 shows a plan view of a bottom component of the cooling system of FIG. 4.

Referring now to FIG. 8, it will be seen that the bottom portion 54 contains a battery-driven air blower or fan unit indicated generally by reference numeral 56, which has at its top a blower air outlet opening 58. The outlet opening 58 mates with an inlet opening 59 at an open lower end 57 of an air duct 60. The open lower end 57 thus communicates through a bottom 55 of the container 52 with the outlet opening 58 of the air blower or fan unit 56.

The air duct 60 extends vertically upwardly through the interior of the container 52 and has, at its upper end, a cooling air discharge outlet in the form of a nozzle 62 which is rotatable relative to the air duct 60. The air outlet nozzle 62 extends through a cover 64, which it is engaged with the top of the container 52 and which serves to close the open top of the container 52.

The cover 64 is formed with an opening 66, through which a drinking tube in the form of a straw 68 to extends downwardly into the interior of the container 52.

Figure 10:
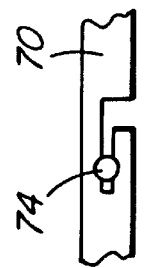
FIG. 10 shows a broken-away view of a locking device forming a part of the cooling system of FIGS. 4–8.

At the bottom of the container 52, there is formed a downwardly extending skirt or flange 70 which, as shown in FIG. 10, is formed with an L-shaped slot 72. The slot 72 is one of a pair of slots, which are provided at opposite sides of the container 52 and which are engaged by projections 74 extending inwardly from an annular wall 76 at the top of the bottom portion 54, the slots 72 and the projections 74 being formations which are interengageable for releasably securing the container 52 to the bottom portion 54.

The bottom portion 54, which it is in the form of a plastic molding, has a battery compartment 75 (FIG. 8) which contains batteries 76 (FIG. 5) for powering the air blower 56.

In use of this cooling system, the cover 64 is removed from the container 52, which then has an open top serving as a drink inlet opening, and a chilled beverage 78 is then filled into the container 52 through the open top of the container 52, after which the cover 64 is replaced on the container 52. On operation of the air blower unit 56, air is drawn inwardly through an air inlet opening 80 (FIG. 8) and is discharged upwardly by the air blower unit into the air duct 60. As this air passes through the air duct 60, it flows through a tubular air freshener 65 located in the lower end of the air duct 60. From the air duct 60, the air, which is cooled by the chilled beverage 78 during its upward passage through the air duct 60, is discharged from the air outlet nozzle 62.

When the user of this system desires to consume the chilled drink, he or she can suck the drink through the drinking tube 68. When the beverage 78 has thus been fully consumed, the cover 64, which serves as a lid for the container 52, can be removed from the container 52 in order to enable the container 52 to be re-filled.

Figure 9:
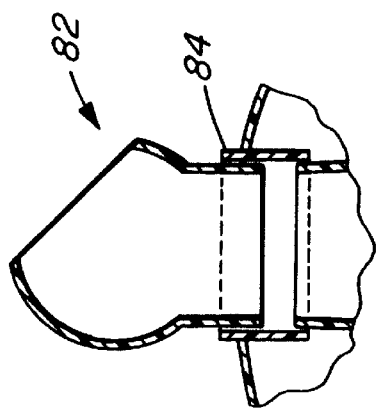
FIG. 9 shows a view, taken in cross-section, of part of a modification of the cooling system of FIGS. 4–8.
Figure 11:
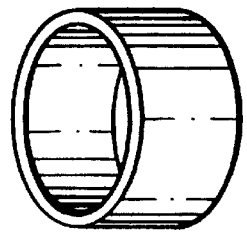
FIG. 11 shows a view in perspective of an air freshener for use in the cooling system of FIGS. 4 to 8.

FIG. 9 shows a modification of the air outlet nozzle 62 of FIG. 8, in the form of a modified, rotatable air outlet nozzle indicated generally by reference numeral 82. This air outlet nozzle 82 is rotatably located in a cylindrical sleeve 84 formed in the top of the cover 64. On rotation of the air outlet nozzle 82, the user can vary the direction of discharge of the cooled air from the cooling system.

Figure 12:
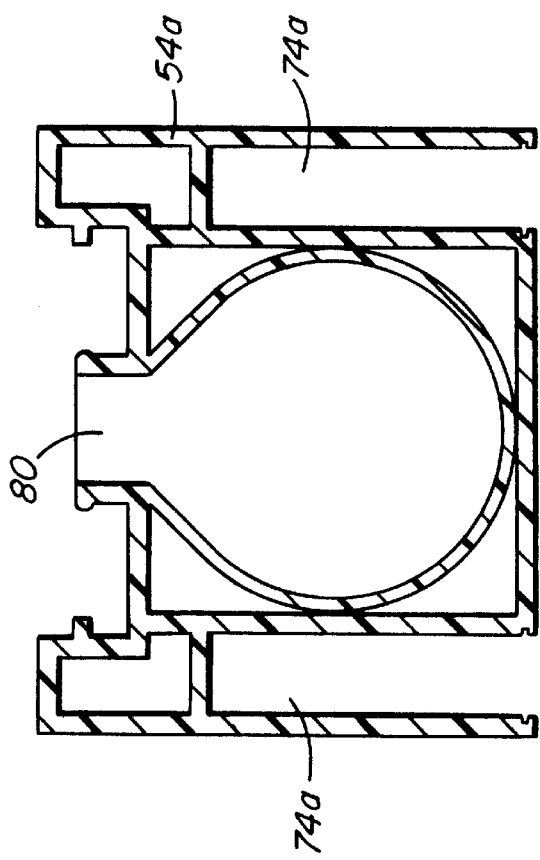
FIG. 12 shows a view taken in horizontal cross-section through a mofification of the bottom portion of the cooling system of FIG. 4.
Figure 13:
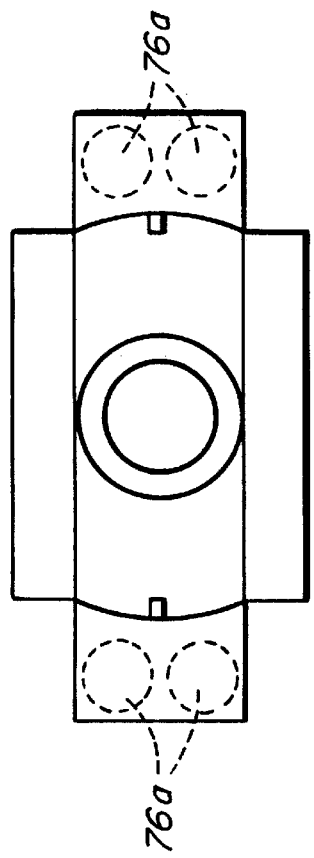
FIG. 13 shows a view in side elevation of the bottom portion of FIG. 12.

FIGS. 12 and 13 show a modified bottom portion 54a which may be employed in place of the bottom portion 54. The bottom portion 54a has two battery compartments 75a for two pairs of batteries 76a.

As will be apparent to those skilled in the art, various further modification may be made in the above-described apparatus within the scope of the appended claims.

I claim:

1. A portable cooling system, comprising:
    a beverage container, said beverage container having a top and a bottom and defining a space for containing a beverage;
    a base unit beneath said container;
    said base unit containing a battery-driven air blower;
    said battery-driven blower having an air outlet opening communicating with said space;
    an inlet opening in said top of said container; and
    a removable cover closing said opening;
    said cover having a beverage outlet opening.

2. A portable cooling system as claimed in claim 1, including an air duct extending upwardly through said space from said bottom of said container, said air outlet opening communicating with said air duct.

3. A portable cooling system as claimed in claim 1, including an air freshener material in said air duct.

4. A portable cooling system as claimed in claim 1, including interengageable formations on said bottom of said container and on said base unit for releasibly securing said base unit to said container.

5. A portable cooling system as claimed in claim 1, including a cooled air discharge outlet, said cooled air discharge outlet comprising a nozzle rotatably mounted in said cover.

6. A portable cooling system as claimed in claim 1, wherein said container has a cooled air discharge outlet separate from said beverage outlet.

7. A portable cooling system, comprising:
    a beverage container, said beverage container having a top, a bottom and a cooled air discharge outlet at said top and said container defining a space for containing a beverage;
    an air duct extending through said space; and
    a battery-driven air blower;
    said battery-driven blower having a blower air outlet opening communicating with said air duct and said air duct communicating with said cooled air discharge outlet; and
    said container including an inlet opening in said top of said container and a removable cover closing said opening and said cooled air discharge outlet comprising a nozzle rotatably mounted in said cover.

8. A portable cooling system as claimed in claim 7, wherein said air duct extends upwardly from said bottom of said container to said cooling air outlet.

9. A portable cooling system, comprising:
    a beverage container, said beverage container having a top and a bottom and defining a space for containing a beverage;

a battery driven air blower; and said battery-driven blower having a blower air outlet opening communicating with said space;

said container having a cooled air discharge outlet and a beverage outlet separate from said cooled air discharge outlet;

said container having a beverage inlet opening and a cover closing said beverage inlet opening; and said cooled air discharge outlet comprising a nozzle rotatably mounted in said cover.

10. A portable cooling system, comprising:

a beverage container, said beverage container having a top and a bottom and defining a space for containing a beverage;

an air duct extending through said space; and a base unit beneath said container;

said base unit containing a battery-driven air blower;

said battery-driven blower having a blower air outlet opening communicating with said air duct;

said container having a cooled air discharge outlet and a beverage outlet separate from said cooled air discharge outlet;

said air duct communicating with said cooled air discharge outlet;

said container including an inlet opening in said top of said container and a removable cover closing said opening; and said beverage outlet opening and said cooled air discharge outlet being provided in said cover.

11. A portable cooling system as claimed in claim 10, wherein said air duct extends through said bottom of said container to said cooled air discharge outlet.

12. A portable cooling system as claimed in claim 10, including interengageable formations on said bottom of said container and on said base unit for releasibly securing said base unit to said container.

13. A portable cooling system as claimed in claim 10, wherein said cooled air discharge outlet comprises a nozzle rotatably mounted in said cover.

14. A portable cooling system as claimed in claim 10, including an air freshener material in said air duct.

* * * * *